(12) United States Patent
Ostroff

(10) Patent No.: US 7,877,139 B2
(45) Date of Patent: Jan. 25, 2011

(54) METHOD AND DEVICE FOR IMPLANTABLE CARDIAC STIMULUS DEVICE LEAD IMPEDANCE MEASUREMENT

(75) Inventor: Alan H. Ostroff, San Clemente, CA (US)

(73) Assignee: Cameron Health, Inc., San Clemente, CA (US)

( * ) Notice: Subject to any disclaimer, the term of this patent is extended or adjusted under 35 U.S.C. 154(b) by 1160 days.

(21) Appl. No.: 11/525,497

(22) Filed: Sep. 22, 2006

(65) Prior Publication Data

US 2008/0077189 A1  Mar. 27, 2008

(51) Int. Cl.
*A61N 1/39* (2006.01)

(52) U.S. Cl. ............................... 607/8; 607/5

(58) Field of Classification Search ............ 607/5–8, 607/27–28; 324/526, 610
See application file for complete search history.

(56) References Cited

U.S. PATENT DOCUMENTS

| | | |
|---|---|---|
| 3,653,387 A | 4/1972 | Ceier |
| 3,710,374 A | 1/1973 | Kelly |
| 3,911,925 A | 10/1975 | Tillery, Jr. |
| 4,030,509 A | 6/1977 | Heilman et al. |
| 4,157,720 A | 6/1979 | Greatbatch |
| 4,164,946 A | 8/1979 | Langer |
| 4,184,493 A | 1/1980 | Langer et al. |
| 4,191,942 A | 3/1980 | Long |
| 4,210,149 A | 7/1980 | Heilman et al. |
| RE30,387 E | 8/1980 | Denniston, III et al. |
| 4,223,678 A | 9/1980 | Langer et al. |
| 4,248,237 A | 2/1981 | Kenny |
| 4,254,775 A | 3/1981 | Langer |
| 4,291,707 A | 9/1981 | Heilman et al. |
| 4,300,567 A | 11/1981 | Kolenik et al. |
| 4,314,095 A | 2/1982 | Moore et al. |
| 4,375,817 A | 3/1983 | Engle et al. |
| 4,402,322 A | 9/1983 | Duggan |
| 4,407,288 A | 10/1983 | Langer et al. |
| 4,424,818 A | 1/1984 | Doring et al. |
| 4,450,527 A | 5/1984 | Sramek |
| 4,548,209 A | 10/1985 | Wielders et al. |
| 4,567,900 A | 2/1986 | Moore |

(Continued)

FOREIGN PATENT DOCUMENTS

DE  298 01 807 U1  7/1998

(Continued)

OTHER PUBLICATIONS

Bardy, Gust H. et al., "Multicenter Experience with a Pectoral Unipolar Implantable Cardioverter-Defibrillator," *JACC*, Aug. 1996, vol. 28, No. 2, pp. 400-410.

(Continued)

*Primary Examiner*—Niketa I Patel
*Assistant Examiner*—Joseph Stoklosa
(74) *Attorney, Agent, or Firm*—Pramudji Law Group PLLC; Ari Pramudji; Mark Schroeder

(57) ABSTRACT

Methods and devices for testing lead impedance in an implantable cardiac stimulus device. A resistor is placed in series with the lead impedance, and a predetermined or known voltage is applied to the resistor and lead impedance. The voltage across the resistor is measured, and it is then determined whether the lead impedance falls within an acceptable range.

11 Claims, 6 Drawing Sheets

U.S. PATENT DOCUMENTS

| | | | |
|---|---|---|---|
| 4,595,009 A | 6/1986 | Leinders | |
| 4,602,637 A | 7/1986 | Elmqvist et al. | |
| 4,603,705 A | 8/1986 | Speicher et al. | |
| 4,693,253 A | 9/1987 | Adams | |
| 4,727,877 A | 3/1988 | Kallok | |
| 4,750,494 A | 6/1988 | King | |
| 4,765,341 A | 8/1988 | Mower et al. | |
| 4,768,512 A | 9/1988 | Imran | |
| 4,800,883 A | 1/1989 | Winstrom | |
| 4,830,005 A | 5/1989 | Woskow | |
| 4,944,300 A | 7/1990 | Saksena | |
| 5,014,697 A * | 5/1991 | Pless et al. | 607/7 |
| 5,044,374 A | 9/1991 | Lindemans et al. | |
| 5,105,810 A | 4/1992 | Collins et al. | |
| 5,105,826 A | 4/1992 | Smits et al. | |
| 5,109,842 A | 5/1992 | Adinolfi | |
| 5,129,392 A | 7/1992 | Bardy et al. | |
| 5,133,353 A | 7/1992 | Hauser | |
| 5,144,946 A | 9/1992 | Weinberg et al. | |
| 5,163,428 A * | 11/1992 | Pless | 607/5 |
| 5,184,616 A | 2/1993 | Weiss | |
| 5,191,901 A | 3/1993 | Dahl et al. | |
| 5,201,865 A * | 4/1993 | Kuehn | 607/8 |
| 5,203,348 A | 4/1993 | Dahl et al. | |
| 5,215,081 A | 6/1993 | Ostroff | |
| 5,230,337 A | 7/1993 | Dahl et al. | |
| 5,255,692 A | 10/1993 | Neubauer et al. | |
| 5,261,400 A | 11/1993 | Bardy | |
| 5,300,106 A | 4/1994 | Dahl et al. | |
| 5,313,953 A | 5/1994 | Yomtov et al. | |
| 5,331,966 A | 7/1994 | Bennett et al. | |
| 5,342,407 A | 8/1994 | Dahl et al. | |
| 5,366,496 A | 11/1994 | Dahl et al. | |
| 5,376,103 A | 12/1994 | Anderson et al. | |
| 5,376,104 A | 12/1994 | Sakai et al. | |
| 5,385,574 A | 1/1995 | Hauser et al. | |
| 5,391,200 A | 2/1995 | KenKnight et al. | |
| 5,405,363 A | 4/1995 | Kroll et al. | |
| 5,411,539 A | 5/1995 | Neisz | |
| 5,411,547 A | 5/1995 | Causey, III | |
| 5,413,591 A | 5/1995 | Knoll | |
| 5,423,326 A | 6/1995 | Wang et al. | |
| 5,425,748 A * | 6/1995 | Pless | 607/5 |
| 5,439,485 A | 8/1995 | Mar et al. | |
| 5,447,521 A | 9/1995 | Anderson et al. | |
| 5,453,698 A | 9/1995 | Williams et al. | |
| 5,476,503 A | 12/1995 | Yang | |
| 5,509,923 A | 4/1996 | Middleman et al. | |
| 5,509,928 A | 4/1996 | Acken | |
| 5,531,765 A | 7/1996 | Pless | |
| 5,531,766 A | 7/1996 | Kroll et al. | |
| 5,534,019 A | 7/1996 | Paspa | |
| 5,534,022 A | 7/1996 | Hoffmann et al. | |
| 5,549,646 A | 8/1996 | Katz et al. | |
| 5,591,213 A | 1/1997 | Morgan | |
| 5,597,956 A | 1/1997 | Ito et al. | |
| 5,601,607 A | 2/1997 | Adams | |
| 5,603,732 A | 2/1997 | Dahl et al. | |
| 5,607,455 A | 3/1997 | Armstrong | |
| 5,618,287 A | 4/1997 | Fogarty et al. | |
| 5,620,477 A | 4/1997 | Pless et al. | |
| 5,643,328 A | 7/1997 | Cooke et al. | |
| 5,645,586 A | 7/1997 | Meltzer | |
| 5,658,317 A | 8/1997 | Haefner et al. | |
| 5,658,319 A | 8/1997 | Kroll | |
| 5,658,321 A | 8/1997 | Fayram et al. | |
| 5,674,260 A | 10/1997 | Weinberg | |
| 5,690,648 A | 11/1997 | Fogarty et al. | |
| 5,690,683 A | 11/1997 | Haefner et al. | |
| 5,697,953 A | 12/1997 | Kroll et al. | |
| 5,713,926 A | 2/1998 | Hauser et al. | |
| 5,722,997 A | 3/1998 | Nedungadi et al. | |
| 5,741,311 A | 4/1998 | Mc Venes et al. | |
| 5,755,742 A | 5/1998 | Schuelke et al. | |
| 5,766,226 A | 6/1998 | Pedersen | |
| 5,776,169 A | 7/1998 | Schroeppel | |
| 5,814,088 A | 9/1998 | Paul et al. | |
| 5,814,090 A | 9/1998 | Latterell et al. | |
| 5,827,326 A | 10/1998 | Kroll et al. | |
| 5,836,976 A | 11/1998 | Min et al. | |
| 5,843,132 A | 12/1998 | Ilvento | |
| 5,895,414 A | 4/1999 | Sanchez-Zambrano | |
| 5,904,705 A | 5/1999 | Kroll et al. | |
| 5,919,211 A | 7/1999 | Adams | |
| 5,919,222 A | 7/1999 | Hjelle et al. | |
| 5,925,069 A | 7/1999 | Graves et al. | |
| 5,935,154 A | 8/1999 | Westlund | |
| 5,941,904 A | 8/1999 | Johnston et al. | |
| 5,957,956 A | 9/1999 | Kroll et al. | |
| 6,014,586 A | 1/2000 | Weinberg et al. | |
| 6,016,445 A | 1/2000 | Baura | |
| 6,026,325 A | 2/2000 | Weinberg et al. | |
| 6,058,328 A | 5/2000 | Levine et al. | |
| 6,093,173 A | 7/2000 | Balceta et al. | |
| 6,095,987 A | 8/2000 | Shmulewitz et al. | |
| 6,104,954 A * | 8/2000 | Blunsden | 607/8 |
| H1905 H | 10/2000 | Hill | |
| 6,128,531 A | 10/2000 | Campbell-Smith | |
| 6,144,866 A | 11/2000 | Miesel et al. | |
| 6,144,879 A | 11/2000 | Gray | |
| 6,148,230 A | 11/2000 | KenKnight | |
| 6,161,042 A | 12/2000 | Hartley et al. | |
| 6,185,450 B1 | 2/2001 | Seguine et al. | |
| 6,185,458 B1 * | 2/2001 | Ochs et al. | 607/5 |
| 6,266,567 B1 | 7/2001 | Ishikawa et al. | |
| 6,278,894 B1 | 8/2001 | Salo et al. | |
| 6,280,462 B1 | 8/2001 | Hauser et al. | |
| 6,317,628 B1 * | 11/2001 | Linder et al. | 600/547 |
| 6,317,633 B1 | 11/2001 | Jorgenson et al. | |
| 6,334,071 B1 | 12/2001 | Lu | |
| 6,345,198 B1 | 2/2002 | Mouchawar et al. | |
| 6,411,844 B1 | 6/2002 | Kroll et al. | |
| 6,445,951 B1 | 9/2002 | Mouchawar | |
| 6,473,648 B1 * | 10/2002 | Prutchi et al. | 607/28 |
| 6,564,099 B2 | 5/2003 | Prutchi et al. | |
| 6,597,950 B2 | 7/2003 | Linder et al. | |
| 6,620,186 B2 | 9/2003 | Saphon et al. | |
| 6,647,292 B1 | 11/2003 | Bardy et al. | |
| 6,721,597 B1 | 4/2004 | Bardy et al. | |
| 6,721,600 B2 | 4/2004 | Jorgenson et al. | |
| 6,754,528 B2 | 6/2004 | Bardy et al. | |
| 6,778,860 B2 | 8/2004 | Ostroff et al. | |
| 6,788,974 B2 | 9/2004 | Bardy et al. | |
| 6,834,204 B2 | 12/2004 | Ostroff et al. | |
| 6,856,835 B2 | 2/2005 | Bardy et al. | |
| 6,865,417 B2 | 3/2005 | Rissmann et al. | |
| 6,866,044 B2 | 3/2005 | Bardy et al. | |
| 6,927,721 B2 | 8/2005 | Ostroff et al. | |
| 6,937,907 B2 | 8/2005 | Bardy et al. | |
| 6,950,705 B2 | 9/2005 | Bardy et al. | |
| 6,952,608 B2 | 10/2005 | Ostroff | |
| 6,952,610 B2 | 10/2005 | Bardy et al. | |
| 6,954,670 B2 | 10/2005 | Ostroff | |
| 6,980,856 B2 | 12/2005 | Sullivan et al. | |
| 6,988,003 B2 | 1/2006 | Bardy et al. | |
| 6,996,434 B2 | 2/2006 | Marcovecchio et al. | |
| 7,020,523 B1 | 3/2006 | Lu et al. | |
| 7,027,858 B2 | 4/2006 | Cao et al. | |
| 7,039,459 B2 | 5/2006 | Bardy et al. | |
| 7,039,463 B2 | 5/2006 | Marcovecchio | |
| 7,043,299 B2 | 5/2006 | Erlinger et al. | |
| 7,062,329 B2 | 6/2006 | Ostroff | |
| 7,065,407 B2 | 6/2006 | Bardy et al. | |
| 7,065,410 B2 | 6/2006 | Bardy et al. | |

| | | | |
|---|---|---|---|
| 7,069,080 B2 | 6/2006 | Bardy et al. | |
| 7,076,294 B2 | 7/2006 | Bardy et al. | |
| 7,076,296 B2 | 7/2006 | Rissmann et al. | |
| 7,090,682 B2 | 8/2006 | Sanders et al. | |
| 7,092,754 B2 | 8/2006 | Bardy et al. | |
| 2004/0254611 A1 | 12/2004 | Palreddy et al. | |
| 2004/0254613 A1 | 12/2004 | Ostroff et al. | |
| 2005/0049644 A1 | 3/2005 | Warren et al. | |
| 2006/0085038 A1 | 4/2006 | Linder et al. | |

FOREIGN PATENT DOCUMENTS

| | | |
|---|---|---|
| DE | 20 2004 016350 U1 | 3/2005 |
| EP | 0 095 727 A1 | 12/1983 |
| EP | 0 316 616 A2 | 5/1989 |
| EP | 0 347 353 A1 | 12/1989 |
| EP | 0 517 494 B1 | 12/1992 |
| EP | 0 518 599 A2 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A2 | 3/1995 |
| EP | 0 677 301 A1 | 10/1995 |
| EP | 0 917 887 A1 | 5/1999 |
| EP | 0 923 130 A1 | 6/1999 |
| EP | 1 000 634 A1 | 5/2000 |
| WO | WO 93/19809 A1 | 10/1993 |
| WO | WO 97/29802 A2 | 8/1997 |
| WO | WO 98/25349 A1 | 6/1998 |
| WO | 98 042406 A1 | 10/1998 |
| WO | WO 99/03534 A1 | 1/1999 |
| WO | WO 99/37362 A1 | 7/1999 |
| WO | WO 99/53991 A1 | 10/1999 |
| WO | 00 043065 A1 | 7/2000 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A2 | 3/2002 |
| WO | WO 02/24275 A2 | 3/2002 |
| WO | WO 02/068046 A1 | 9/2002 |
| WO | WO 03/018121 A2 | 3/2003 |
| WO | 03 053518 A1 | 7/2003 |

OTHER PUBLICATIONS

Friedman, Richard A. et al., "Implantable Defibrillators In Children: From Whence to Shock," *Journal of Cardiovascular Electrophysiology*, vol. 12, No. 3, Mar. 2001, pp. 361-362.

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356-360.

Higgins, Steven L. et al., "The First Year Experience with the Dual Chamber ICD," *PACE*, Jan. 2000, vol. 23, pp. 18-25.

Mirowski, M. et al., "Automatic Detection and Defibrillation of Lethal Arrhythmias-A New Concept," *JAMA*, vol. 213, No. 4, Jul. 27, 1970, pp. 615-616.

Olson, Walter H. et al., "Onset and Stability for Ventricular Tachyarrhythmia Detection in an Implantable Pacer-Cardioverter-Defibrillator," *IEEE*, (1987) pp. 167-170.

Schuder, John C., "Completely Implanted Defibrillator," *JAMA*, vol. 214, No. 6, Nov. 9, 1970, p. 1123 (single sheet).

Schuder, John C. et al., "Experimental Ventricular Defibrillation with an Automatic and Completely Implanted System," *Trans. Amer. Soc. Artif. Int. Organs*, vol. XVI (1970) pp. 207-212.

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95-124.

Schuder, John C. et al., "Standby Implanted Defibrillators," *Arch Intern. Med*, vol. 127, Feb. 1971, p. 317 (single sheet).

Schuder, John C. et al., "Transthoracic Ventricular Defibrillation in the Dog with Truncated and Untruncated Exponential Stimuli," *IEEE Transactions on Bio-Medical Engineering*, vol. BME-18, No. 6, Nov. 1971, pp. 410-415.

Schwacke, H. et al., "Komplikationen mit Sonden bei 340 Patienten mit einem Implantierbaren Kardioverter/Defibrillator," *Z Kardiol* (1999)vol. 88, No. 8, pp. 559-565.

Throne, Robert D., "A Comparison of Four New Time-Domain Techniques for Discriminating Monomorphic Ventricular Tachycardia from Sinus Rhythm Using Ventricular Waveform Morphology," *IEEE Transactions on Biomedical Engineering*, vol. 38, No. 6, Jun. 1991, pp. 561-570.

Tietze U. et al., "Halbleiter-Schaltungstechnik," © Springer-Verlag (Berlin, Germany), (1991), pp. 784-786.

Valenzuela, Terrence D. et al., "Outcomes of Rapid Defibrillation by Security Officers After Cardiac Arrest in Casinos," *The New England Journal of Medicine*, Oct. 26, 2000, vol. 343, No. 17, pp. 1206-1209.

Walters, R.A. et al., "Analog to Digital Conversion International Conference of the IEEE Engineering in Techniques in Implantable Devices," *Annual International Conference of the IEEE Engineering in Medicine and Biology Society*, vol. 13 No. 4 (1991) p. 1674-1676.

* cited by examiner

METHOD AND DEVICE FOR IMPLANTABLE CARDIAC STIMULUS DEVICE LEAD IMPEDANCE MEASUREMENT

FIELD

The present invention is related to the field of implantable medical devices. More specifically, the present invention relates to lead impedance measurement for implantable cardiac stimulation devices.

BACKGROUND

An implantable cardiac stimulus device is shown in FIG. 1. The device 10 includes a canister 12 that houses electronics for controlling electrical cardiac stimulation. An electrode 14 may optionally be placed on the canister 12, and a lead 16 extends from the canister 12 and carries one or more lead electrodes 18, 20. The device may be suited for delivery of cardiac stimulus as a pacing device providing low energy pulses timed to help regularize cardiac function, or may be suited instead for delivery of higher energy pulses to convert a malignant cardiac event to normal sinus rhythm. When properly implanted and properly functioning, impedances between pairs of electrodes 14, 18, 20 will generally fall within a known range. When the measured impedance falls outside the known range, it can often be determined that something is wrong and, possibly, that the device should be explanted and replaced. The device 10 may include telemetry circuitry/devices allowing it to communicate from an implanted position with an associated programmer. Such communication may include annunciation of a lead impedance measurement that is outside of an expected range. The impedance may fall out of range for any number of reasons, for example, device failure, improper lead position, or anatomical abnormality. Lead impedance measurement is therefore a desirable function of such implantable medical devices.

SUMMARY

The present invention, in illustrative embodiments, includes methods and devices equipped and configured for testing lead impedance in an implantable cardiac stimulus device. In an illustrative method, a device is provided having a resistor is placed in series with a lead impedance for testing. In the illustrative method, a predetermined or known voltage is applied to the resistor and lead impedance, and the voltage across the resistor is measured. In the illustrative method, it is then determined whether the lead impedance falls within an acceptable range. Devices equipped and configured for performing like methods make additional illustrative embodiments.

DETAILED DESCRIPTION

The following detailed description should be read with reference to the drawings. The drawings, which are not necessarily to scale, depict illustrative embodiments and are not intended to limit the scope of the invention.

As used herein, "lead impedance" may include several components. For example, lead impedance may include impedance of a connection between circuitry and a first electrode, first electrode impedance, interface impedance between the first electrode and patient tissue, patient impedance between the first electrode and a second electrode, interface impedance between patient tissue and the second electrode, second electrode impedance, and/or the impedance of a connection between circuitry and the second electrode. Typical values for lead impedance will vary from one device and implantation method to another. For example, conventional devices have heretofore made use of epicardial, transvenous, and/or cardiac electrodes. Some new devices will make use of subcutaneous electrodes having different spacings and crossing different tissue components. Examples of methods and devices for, and associated with, subcutaneous placement are illustrated in U.S. Pat. Nos. 6,788,974; 6,754,528; 6,721,597; and 6,647,292, which are assigned to the assignee of the present invention and which are all incorporated herein by reference.

In some embodiments, the present invention will be incorporated into an implantable cardioverter-defibrillator (ICD). Other embodiments may also be used or incorporated into pacemakers or other electrical stimulus supplying devices. While the following generally discusses lead impedance, it is also contemplated that impedance between any two electrodes of an implantable stimulus system may be measured, for example, in a unitary stimulus system. One example in the cardiac context is that disclosed in commonly assigned U.S. Pat. No. 6,647,292, the disclosure of which is incorporated herein by reference.

Figure 2:
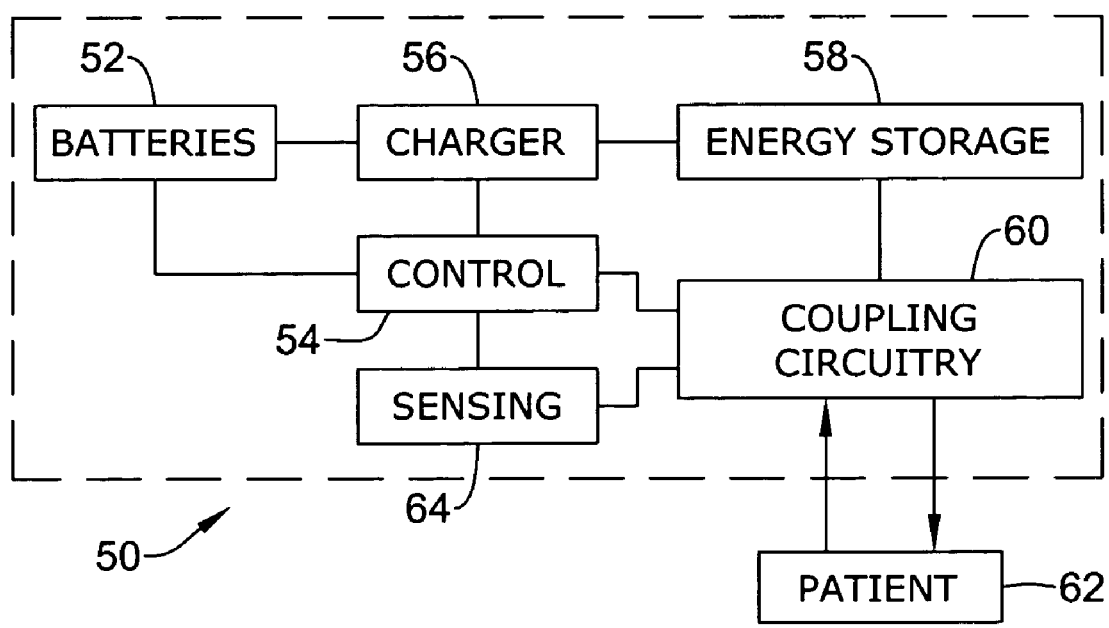
FIG. 2 is a block schematic for an implantable cardiac stimulus device.

FIG. 2 is a block schematic for an implantable cardiac stimulus device that is configured as an ICD. The ICD 50 typically includes batteries 52 that power a control block 54, which may include a microcontroller, logic, or the like. The control block 54 is coupled to a charger 56 that is used to relay power from the batteries 52 to energy storage 58. Energy storage 58 is a temporary energy storage system that may include one or more capacitors. The charger 56 is used to step up the voltage supplied by the batteries 52 (typically in the range of a few volts) to a voltage more suitable for defibrillation (often on the order of hundreds of volts), and store this energy at the higher voltage in the energy storage 58. The energy storage 58 is electrically connected to coupling circuitry 60 that is used to connect with the patient 62. Sensing circuitry 64 is also connected to the coupling circuitry 60, and is used by the control block 54 to determine whether defibrillation is needed. The sensing circuitry 64 may include suitable circuitry and circuit elements for amplifying, filtering, and/or analysis of cardiac signals. Not shown, though often included, is additional circuitry used to discharge any excess charge on the energy storage 58, for example, after delivery of a stimulus.

The typical operation of an ICD for defibrillation includes the following. First, the control block 54 determines, using the sensing circuitry 64, that defibrillation is needed due to the occurrence of a malignant cardiac condition. Next, the control block 54 causes the charger 56 to begin charging the energy storage 58. Once the energy storage 58 is charged to a desired level or for a predetermined time, the control block 54 causes the coupling circuitry 60 to discharge the energy storage 58 to the patient 62.

The present invention may be incorporated into an ICD, into an implantable pacing device, or into a hybrid device having both ICD and pacemaker features. For pacemaker functions, the delivered stimulus energy will be much lower than that of an ICD, such that the charger 56 and/or energy storage 58 shown in FIG. 2 may be omitted, simplified, or bypassed.

Figure 3:
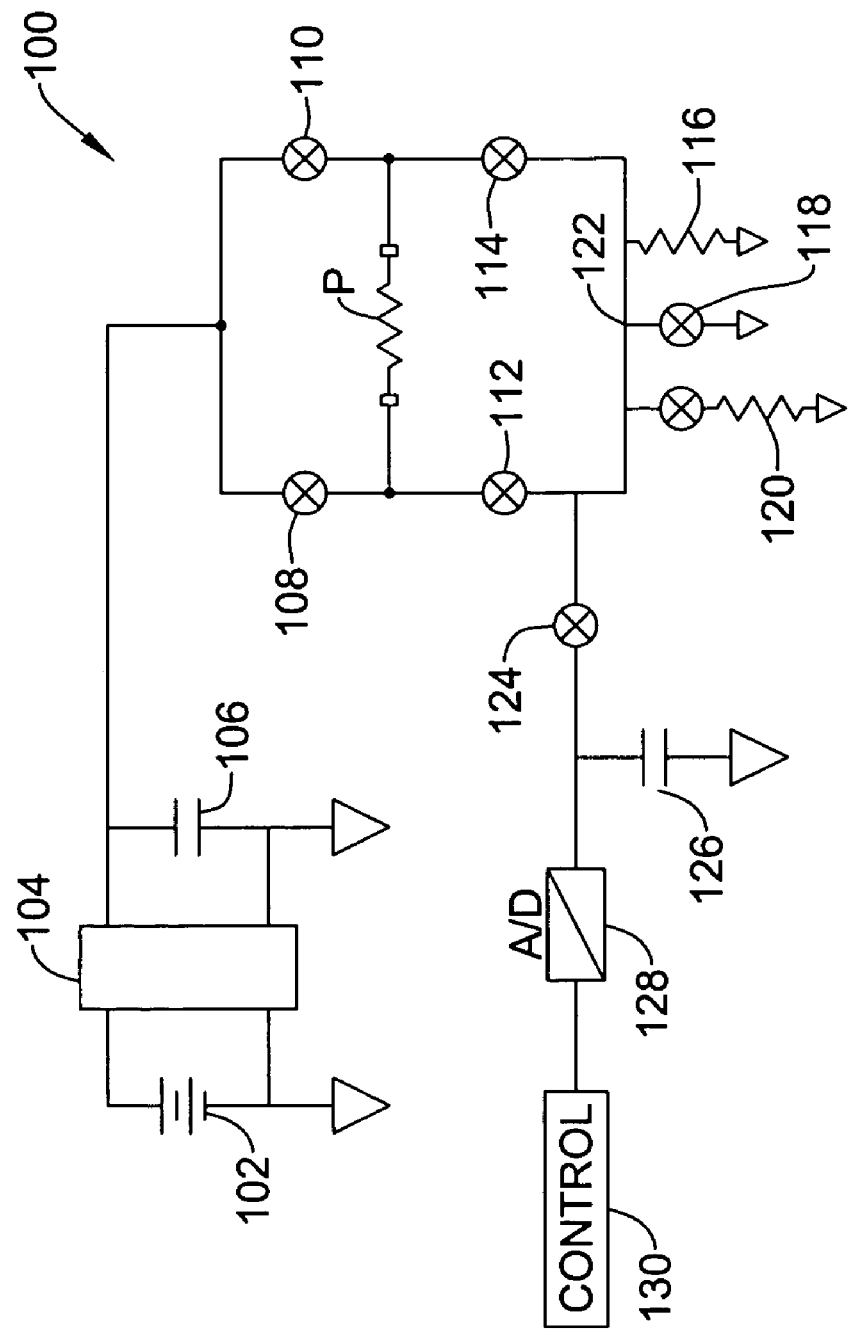
FIG. 3 is a schematic diagram for an illustrative embodiment.

FIG. 3 is a schematic diagram for an illustrative embodiment. The illustrative embodiment is shown in the form of an ICD-pacemaker hybrid device having an H-bridge configuration. The circuit 100 includes a battery 102 coupled via a charger 104 to a capacitance shown as power capacitor 106. It should be understood that the power capacitor 106 may be a single device or may be any suitable configuration of several capacitors and/or other suitable devices.

The power capacitor 106 is coupled to an H-bridge having a first high side switch 108 and a second high side switch 110 which couple to a patient via electrodes, with the patient shown schematically as a resistor P. The H-bridge further includes low side switches 112, 114. The switches 108, 110, 112, 114 may take any suitable form such as, for example, silicon controlled rectifiers (SCR), insulated gate bipolar transistors (IGBT), or MOSFET devices. In some embodiments, transistors, rather than SCR devices, are used for the low side switches 112, 114 to provide for a constant current control during pacing functions and/or fibrillation inducing device efficacy testing. Some further device functionality is set forth in copending U.S. application Ser. No. 11/114,526, filed Apr. 26, 2005, entitled METHODS AND IMPLANTABLE DEVICES FOR INDUCING FIBRILLATION BY ALTERNATING CONSTANT CURRENT, the disclosure of which is incorporated herein by reference.

The circuit 100 further includes three discharge legs. A first leg includes a testing resistor 116. A second leg includes a nonlinear device 118 adapted for use in defibrillation. In an illustrative embodiment, the nonlinear device 118 may be a MOSFET switch. In other embodiments, the nonlinear device 118 may be a different type of switch, or it may be a diode or any other device allowing for high current throughput to ground. A third leg includes both a switch and a resistor and is referred to herein as a constant current leg 120. The constant current leg 120 can be used to provide a feedback circuit that may be used to make the low side switches 112, 114 functional for current controlling circuits, as set forth in U.S. Pat. No. 6,952,608, the disclosure of which is incorporated herein by reference.

Each of the three discharge legs connects together at node 122 which is shown connected to a lead impedance testing circuit. A switch 124 in combination with a capacitor 126 makes a sample and hold circuit, the output of which is coupled into an analog-to-digital converter 128 that provides a digital signal indicative of a sampled voltage to control block 130. If desired, the converter 128 and control block 130 may both be part of a microcontroller.

During operation, several modes are available for circuit 100. In a defibrillation mode, high side switches 108, 110 remain open while the power capacitor 106 is charged from the battery 102 by charger 104 to a stimulation level that may be set to a suitable level; typical levels range into the hundreds of volts but vary from device to device. Once the power capacitor 106 is charged to the desired level, a high side switch and a low side switch each close to allow stimulus to reach the patient P, with delivery combinations including switches 108/114 or switches 110/112. The defibrillation current then reaches node 122, where it passes primarily through the non-linear device 118. If the non-linear device 118 is a switch, it may be closed, grounding node 122. If the non-linear device 118 is a diode, then node 122 is held at the diode threshold voltage, such that some current may pass through one of the other legs while the major portion of current passes through the non-linear device. For example, if a one-amp pulse of current is applied for defibrillation and the resistance from node 122 to ground is 33 ohms and the non-linear device is a diode having a 0.7 V threshold, approximately 21 mA of current goes through the resistor, while the rest of the current goes through the non-linear device.

In a constant-current pacing mode, the switch in the constant current leg 120 is closed. Feedback may be used to control current by adjusting the base voltage supplied to switches 112, 114 if such switches are supplied as IGBT devices, or the gate voltage if such switches are MOSFET devices. Some methods of using such feedback are set forth in U.S. Pat. No. 6,952,608, the disclosure of which is incorporated herein by reference.

In a testing mode, the switch in the constant current leg 120 is open. If a switch is used as non-linear device 118, that switch remains open as well. As further explained below, if the voltages used, particularly the voltage at node 122, remain low enough, a diode used as non-linear device 118 will act as an open circuit. For the testing mode, the capacitor 106 is charged to a predetermined testing level using the battery 102 and charger 104. The testing level may be selected to avoid providing a stimulus to the patient that is noticed by the patient or which modifies cardiac function. When the testing level is reached, an appropriate combination of H-bridge switches is closed (either switches 108/114 or switches 110/112) to apply the testing pulse to the patient P. The current then crosses testing resistor 116. Meanwhile, sampling switch 124 is closed, causing capacitor 126 to sample the voltage at node 122. Prior to the end of the testing pulse, the sampling switch 124 is opened, holding the sampled voltage. Converter 128 is used to convert the sampled voltage to a digital signal for use by the control 130.

Because the testing voltage is known and predetermined, the combination of the patient resistance P and the testing resistor 116 creates a primarily resistive voltage divider. The patient resistance P is simplified for the purpose of illustration, as it may include impedances that are resistive and reactive, and includes any impedance encountered when current goes from the circuit 100 through lines connecting (sometimes through leads) to the electrodes, which in turn couple to and through patient tissue. By knowing the total voltage drop, the size of the testing resistor 116, and the voltage at node 122, the following formula may be used to calculate the lead impedance:

$$(R_L+R_T)/R_T=V_T/V_{122}$$

Where $R_L$ is the lead impedance, $R_T$ is the testing resistor 116 resistance, $V_T$ is the applied testing voltage, and $V_{122}$ is the voltage sampled at node 122. For example, if the applied voltage $V_T$ is 3 Volts, and the sampled voltage is 0.48 Volts, with $R_T$ being 33 ohms, then the lead impedance would be about 173 ohms.

The above numerical example also shows that a diode having a threshold voltage of 0.6-0.7 volts, for example, could be used as the non-linear device 118, since the sampled voltage at node 122 is less than the diode threshold.

While the above may be used to "calculate" the lead impedance, the inclusion of a number of switches in the circuitry means that there may be some difficulty in exactly specifying the actual impedance. The use of a capacitor to provide the voltage pulse means that the pulse itself degrades with time, while the use of a capacitor to sample the voltage means there is some time constant involved in the sampling method, which may also pose difficulties in exact calculation. However, if an expected range of impedances is defined, such as a range between 75-225 ohms for a subcutaneous device, this range may be used to determine whether the device is likely operating correctly.

In an illustrative example, the "on-time" of the applied pulse used for testing lead impedance is kept quite short, for example, less than 20 milliseconds. This may be the case, for example, to prevent stimulation of the patient's muscles during lead impedance testing. In such an example, the applied voltage may be modeled as a constant, as there is little time to drain the stored voltage on the power capacitor. In another embodiment, the charging circuitry may be maintained in an active state during application of the testing pulse, preventing significant degradation of the stored voltage.

In some embodiments, a number of test impedances may be used prior to insertion to define acceptable sensed voltage ranges. For example, a header and lead assembly may be coupled to a given canister, and several resistors may be placed between the electrodes prior to insertion for the purpose of testing the device ranges. This may allow calibration of the device for various purposes including lead impedance measurement. For example, a test with a known resistor may be directed by a programmer prior to insertion of the device, and the programmer may then communicate the "actual" impedance of the known resistor to the implantable device, allowing the implantable device to determine an acceptable range based on its internal measurement.

Figure 1:
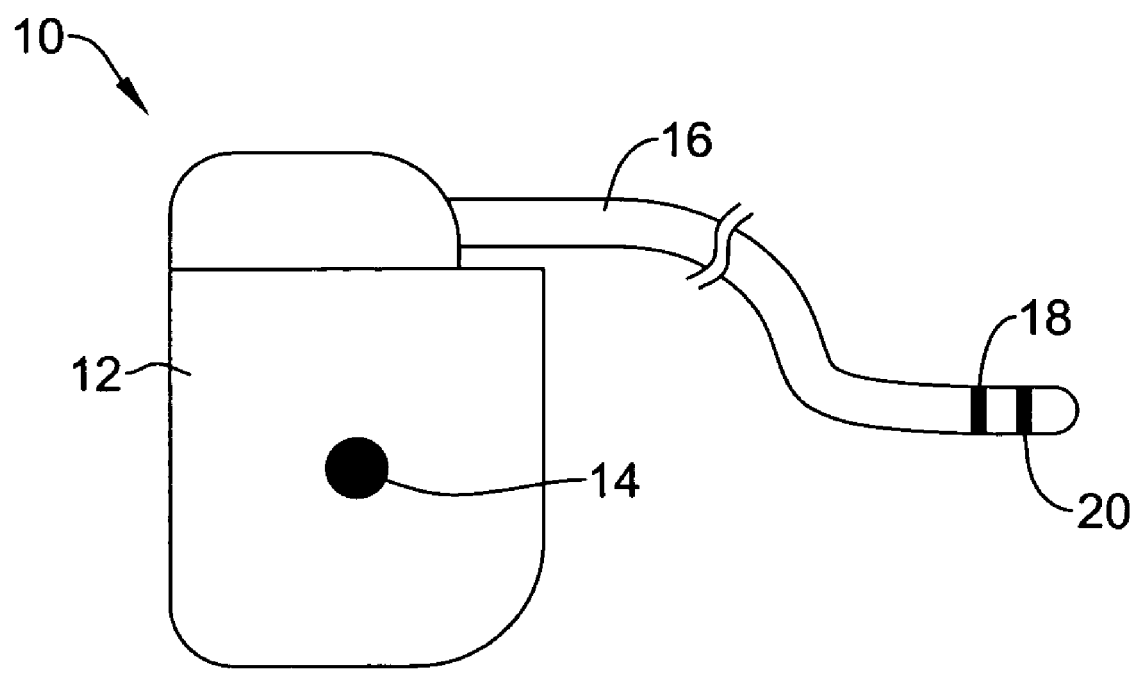
FIG. 1 is a schematic plan view of an implantable cardiac stimulus device including a lead assembly.

In some embodiments, a testing set is provided prior to implantation. More specifically, a device as shown in FIG. 1 may be provided such that the header, which connects the lead 16 to the canister 12, is attachable to the canister 12 prior to implantation. Before implantation and before attachment of the lead 16 and header, a set of testing devices having known impedances may be used to initialize the device. Thus the canister 12 may be coupled to an impedance mimicking a minimum expected impedance for testing purposes, and later coupled to an impedance mimicking a maximum expected impedance for testing purposes. The testing operation may be performed while in each of the configurations, and the sampled voltages noted as corresponding to minimum and maximum lead impedance.

Each of the above methods provides a form of determining whether the lead impedance is acceptable without being an exhaustive list of ways for checking the acceptability of lead impedance.

Figure 4:
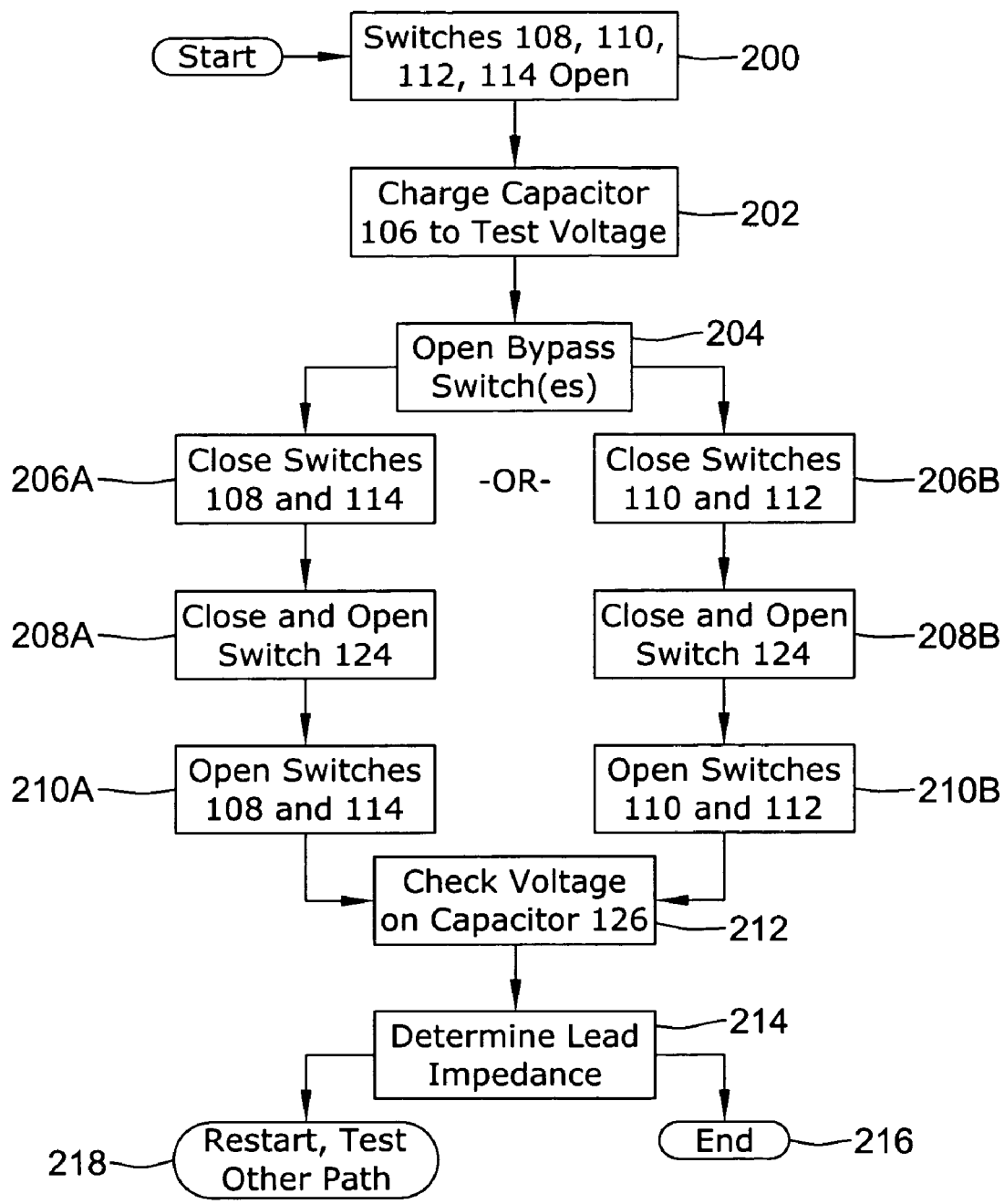
FIG. 4 shows, in block diagram form, an illustrative method embodiment.

FIG. 4 shows, in block diagram form, an illustrative method embodiment. The illustrative method uses reference numerals from FIG. 3. From a start block, the system is in a state as shown at 200 wherein the H-bridge switches are open. Next, the power capacitor is charged, as shown at 202, to a test voltage level. The test voltage may be any appropriate voltage, preferably (though not necessarily) chosen such that the patient will not be aware that testing is occurring and/or such that cardiac function of the patient is uninterrupted. Any bypass switches (included in FIG. 3 but not necessary to the method) are then opened, as shown at 204. At this point, the method may take one of two paths.

In one branch, the method may close a first pair of H-bridge switches, as shown at 206A. Next, a sample is taken by closing and opening a sampling switch, as shown at 208A, after which the H-bridge switches are again opened, as shown at 210A. In the other branch, a second pair of H-bridge switches are opened, as shown at 206B, a sample is taken at 208B, and the H-bridge switches are again opened, as shown at 210B.

Next, the sampled voltage is checked, as shown at 212. The lead impedance may then be determined, as shown at 214, as being either acceptable or unacceptable. In some embodiments, the method ends here, as shown at 216. In other embodiments, the method will restart, as shown at 218, to allow for testing on a different branch. For example, if a first time through the method follows steps 206A, 208A and 210A, the method may recycle at 218 and follow steps 206B, 208B and 210B the next time. This allows for not only checking lead impedance but also making certain that each of the H-bridge switches is operating in an acceptable fashion. Further, the optional step of testing the circuit in both "directions" allows the method to subtract any electrode polarization voltage that could contribute an error term to the calculation of lead impedance if only a single measurement is used.

Figure 5:
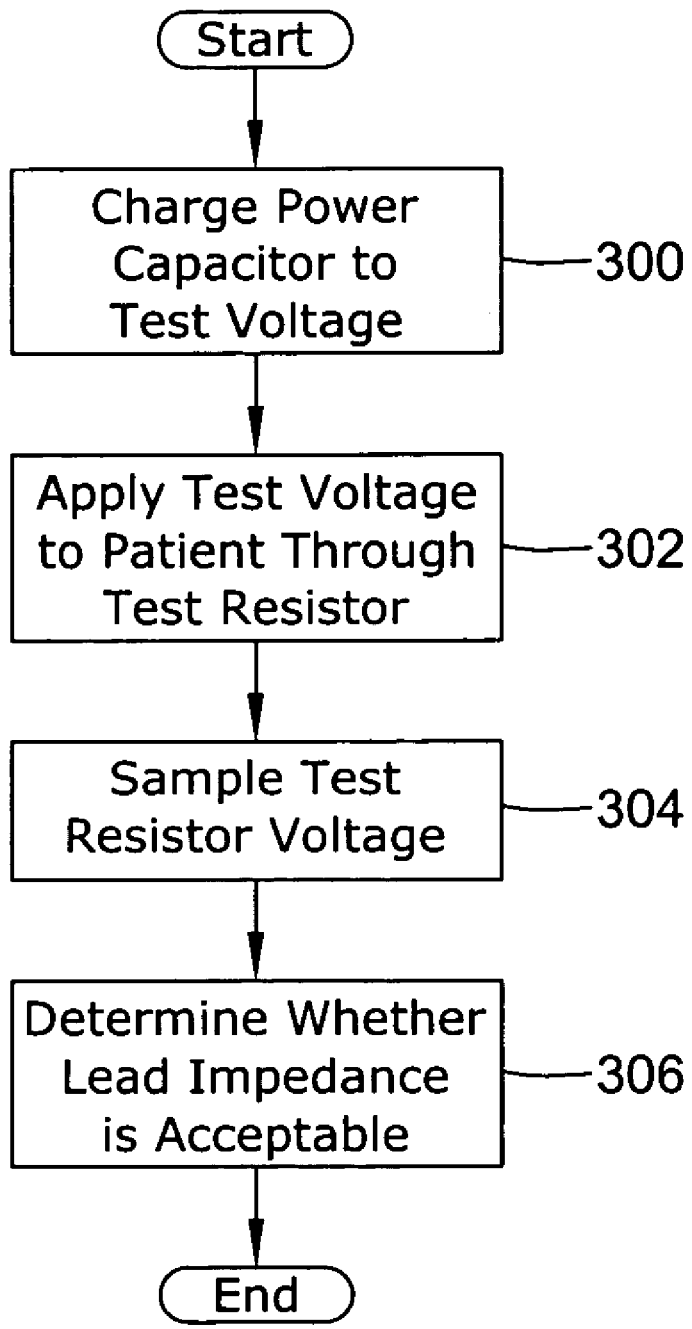
FIG. 5 illustrates another method embodiment in block form.

FIG. 5 illustrates another method embodiment in block form. From a start block, the method includes charging the power capacitor to a test voltage, as shown at 300. Next, the test voltage is delivered to the patient through a test resistor, as shown at 302. The test resistor voltage is sampled while the voltage is being delivered, as shown at 304. Next, it is determined whether the lead impedance is acceptable, as shown at 306. The method of checking lead impedance then ends. If the lead impedance is not acceptable, an error flag may be set by the system controller, or other corrective or annotative action may be taken.

As discussed above, in some embodiments, the sampling step may be performed across a very short interval. In such embodiments, this prevents degradation of the applied voltage from the power capacitor, while also avoiding patient stimulation. If the power capacitor discharges too much during testing, the reading across the test resistor may be reduced due to discharge, rather than attenuation, potentially causing confusion and/or leading to an error. In some embodiments, this effect is avoided by using a test interval shorter than the RC time constant of the power capacitor and test resistor only. In another embodiment, the sampling and/or test interval has a duration less than half the RC time constant of the power capacitor and test resistor only.

Figure 6:
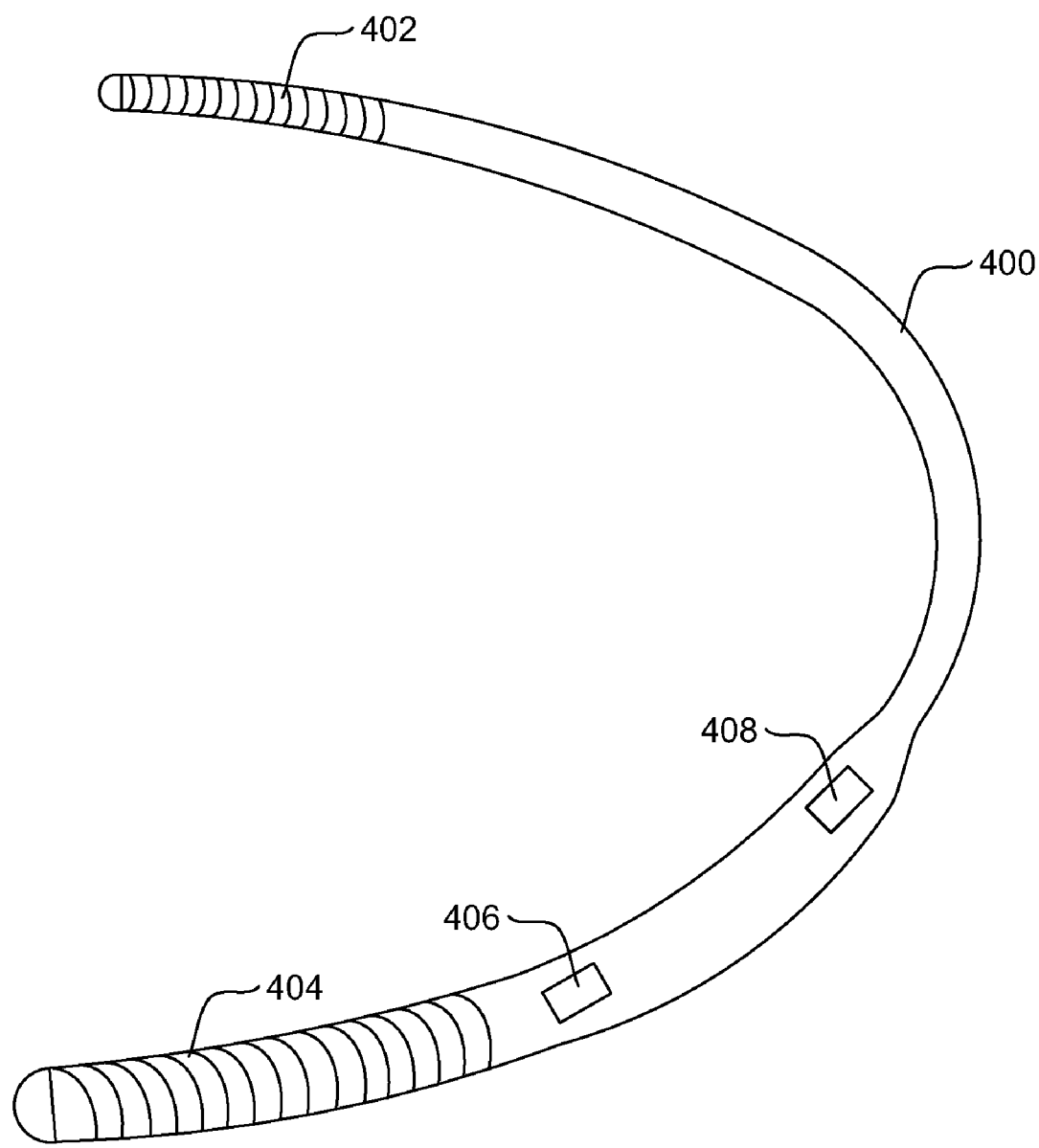
FIG. 6 shows a unitary embodiment.

In another embodiment, a unitary system allows for testing impedance between two electrodes both disposed on the canister or housing of an implantable cardiac stimulation device. FIG. 6 shows a unitary system 400 having electrodes 402, 404, 406, 408 all disposed on a unitary canister, in this embodiment without a separate lead. Impedance may be tested between any of the electrodes 402, 404, 406, 408. The device as shown in FIG. 6 may be implanted as described, for example, in U.S. Pat. No. 6,647,292.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An implantable cardiac stimulation device comprising:
   a first electrode;
   a second electrode;
   a housing containing operational circuitry including:
      a power capacitor for storing stimulation energy;
      charging circuitry for charging the power capacitor;
      control circuitry configured to direct a stimulus operation including charging the power capacitor to a predetermined stimulus voltage and discharging the power capacitor to deliver therapy using at least the first and second electrodes, the control circuitry including a delivery circuit having a high side and a low side, the high side coupling the power capacitor to the first and second electrodes and the low side coupling the first and second electrodes to the testing resistor, the high and low sides each comprising first and second electric switches; and a testing resistor placed such that, when in a testing configuration, a testing current applied between the first and second electrodes passes through the testing resistor;

wherein the control circuitry is further configured to direct a testing operation including charging the power capacitor to a testing voltage and closing a high side switch and a low side switch of the H-bridge to apply current from the power capacitor through the first and second electrodes such that at least some current passing between the first and second electrodes also passes through the testing resistor, the testing voltage being less than the stimulus voltage.

2. The device of claim 1, further comprising a bypass device placed such that, during the stimulus operation, the bypass device is configured to allow stimulus current to bypass the testing resistor during cardiac stimulus.

3. The device of claim 2, wherein the bypass device is a switch, wherein the control circuitry is further configured such that, during the stimulus operation, the bypass switch allows stimulus current to bypass the testing resistor.

4. The device of claim 1, further comprising a sample and hold circuit coupled to the testing resistor to capture a voltage across the testing resistor.

5. The device of claim 4, wherein the sample and hold circuit comprises at least a sampling capacitor and a holding switch.

6. The device of claim 4, wherein the control circuitry is coupled to the sample and hold circuit such that the control circuitry captures a tested voltage sampled and held by the sample and hold circuit.

7. The device of claim 6, wherein the control circuitry is configured to use the tested voltage to find impedance between the first and second electrodes.

8. The device of claim 1, wherein delivery circuit takes the form of an H-bridge and is configured for a first shocking delivery configuration and a second shocking delivery configuration, wherein the control circuitry controls the delivery configurations, and the first and second shocking delivery configurations allow a stored voltage on the power capacitor to be applied in either of two polarities to the first and second electrodes.

9. The device of claim 8, wherein the testing operation includes a first portion for testing impedance of the first shocking delivery configuration and a second portion for testing impedance of the second shocking delivery configuration.

10. The device of claim 1 further comprising a lead electrode assembly on which the first electrode is disposed, wherein the second electrode is disposed on the housing.

11. The device of claim 1 wherein each of the first and second electrodes are placed on the housing.

* * * * *